US012588869B2

(12) United States Patent
Fang et al.

(10) Patent No.: US 12,588,869 B2
(45) Date of Patent: Mar. 31, 2026

(54) METHOD AND APPARATUS PROVIDING AN ONGOING AND REAL TIME INDICATOR FOR SURVIVAL AND MAJOR MEDICAL EVENTS

(71) Applicant: AiCare Corporation, San Jose, CA (US)

(72) Inventors: Fang Fang, Cupertino, CA (US); Xuzhe Zhi, Placentia, CA (US); Raymond Fangkai Xu, Cupertino, CA (US); John Fee, Knoxville, TN (US)

(73) Assignee: AiCare Corporation, San Jose, CA (US)

( * ) Notice: Subject to any disclaimer, the term of this patent is extended or adjusted under 35 U.S.C. 154(b) by 0 days.

(21) Appl. No.: 18/659,779

(22) Filed: May 9, 2024

(65) Prior Publication Data

US 2024/0298965 A1    Sep. 12, 2024

Related U.S. Application Data

(63) Continuation-in-part of application No. 16/900,961, filed on Jun. 14, 2020, now Pat. No. 12,144,657.
(Continued)

(51) Int. Cl.
*A61B 5/00*         (2006.01)
*A61B 5/0205*     (2006.01)
(Continued)

(52) U.S. Cl.
CPC .......... *A61B 5/4857* (2013.01); *A61B 5/0205* (2013.01); *A61B 5/7267* (2013.01);
(Continued)

(58) Field of Classification Search
None
See application file for complete search history.

(56) References Cited

U.S. PATENT DOCUMENTS 5,755,671 A      5/1998  Albrecht et al.
2005/0010254 A1   1/2005  Zhang et al.
(Continued)

OTHER PUBLICATIONS

International Search Report [ISA/US] PCT/US2020/037661 dated Oct. 5, 2020.
(Continued)

*Primary Examiner* — Aurelie H Tu
(74) *Attorney, Agent, or Firm* — Edwin S. Flores; Daniel J. Chalker; Chalker Flores, LLP

(57)                ABSTRACT

Provided herein are methods and devices for determining a personalized circadian rhythm identification and prediction from wearable data comprising: obtaining or having obtained data from one or more wearable devices during one or more daytime and nighttime cycles; using a processor and a machine learning algorithm comprising: determining a daytime threshold and a nighttime threshold from the data obtained during the one or more daytime and nighttime cycles by: temporally segmenting the data; identifying one or more daytime and nighttime boundary by: selecting from at least one of physical activity, heart rate, or sleep status data; temporally segmenting the physical activity, heart rate, or sleep status data to establish a circadian rhythm; using at least one of a 2-mean, 5-mean, or K-nearest neighbor algorithm to determine the one or more daytime and sleep-time boundaries; and identifying and predicting the personalized circadian rhythm.

23 Claims, 9 Drawing Sheets

Related U.S. Application Data

(60) Provisional application No. 62/861,788, filed on Jun. 14, 2019.

(51) Int. Cl.
*G16H 40/67* (2018.01)
*A61B 5/024* (2006.01)
*A61B 5/11* (2006.01)

(52) U.S. Cl.
CPC .......... *G16H 40/67* (2018.01); *A61B 5/02438* (2013.01); *A61B 5/1118* (2013.01); *A61B 5/4809* (2013.01)

(56) References Cited

U.S. PATENT DOCUMENTS

| | | | | |
|---|---|---|---|---|
| 2006/0224047 | A1* | 10/2006 | Suzuki ................. | A61B 5/1118 600/595 |
| 2010/0249645 | A1 | 9/2010 | Semler et al. | |
| 2011/0230790 | A1* | 9/2011 | Kozlov ............... | G04G 13/026 600/595 |
| 2012/0253207 | A1 | 10/2012 | Sarkar et al. | |
| 2013/0018284 | A1* | 1/2013 | Kahn .................... | G04G 21/04 600/595 |
| 2013/0190903 | A1 | 7/2013 | Balakrishnan et al. | |
| 2014/0046144 | A1 | 2/2014 | Jayaraman et al. | |
| 2015/0282766 | A1 | 10/2015 | Cole et al. | |
| 2015/0282767 | A1 | 10/2015 | Stivoric et al. | |
| 2016/0066838 | A1 | 3/2016 | DeCharms | |
| 2017/0094046 | A1* | 3/2017 | Raymann .............. | G08B 21/06 |
| 2017/0312515 | A1 | 11/2017 | Ferree et al. | |
| 2018/0160905 | A1* | 6/2018 | Wang .................. | A61B 5/7246 |
| 2019/0175077 | A1* | 6/2019 | Zhang ................... | G06F 3/017 |

OTHER PUBLICATIONS

Kozina, et al. "Efficient Activity Recognition and Fall Detection Using Accelerometers" Communications in Computer and Information Science • Sep. 2013, DOI: 10.1007/978-3-642-41043-7_2.

* cited by examiner

METHOD AND APPARATUS PROVIDING AN ONGOING AND REAL TIME INDICATOR FOR SURVIVAL AND MAJOR MEDICAL EVENTS

CROSS-REFERENCE TO RELATED APPLICATIONS

This application is a Continuation-in-Part of, and claims priority to, U.S. application Ser. No. 16/900,961, filed Jun. 14, 2020, and claims priority to U.S. Provisional Application Ser. No. 62/861,788, filed Jun. 14, 2019, the entire contents of which are incorporated herein by reference.

TECHNICAL FIELD OF THE INVENTION

The present invention relates in general to the field of methods and devices for providing an ongoing and real time indicator for prediction of survival and major medical events.

STATEMENT OF FEDERALLY FUNDED RESEARCH

None.

BACKGROUND OF THE INVENTION

Without limiting the scope of the invention, its background is described in connection with monitoring and risk prediction for at-home and in-hospital care.

Today many different methods are available for providing a myriad of combinations of healthcare. As is well known, most of the healthcare expenditures occur in a transitional state from healthcare to homecare.

In between those two points, healthcare is relatively expensive. During this period of healthcare transition, most subjects require increased healthcare in order to either improve the quality of life or extend life. In many cases, the subject is admitted to a hospital for a particular condition and is released to either outpatient in-home care or to assisted-living, or hospice.

In the case of in-home care or assisted living, there is a great need to monitor the subject for activity levels to ensure that they are adequately moving around and are performing most daily activities such as eating, going to the restroom, and or other appropriate activities.

Part of the problem is that there is no easy method to monitor their activity. Most activity monitoring is done either with video cameras or in home archaic care assistance or other such inferior methods.

These monitoring methods can be time-consuming, and in the case of the video system, the caretaker would need to daily and hourly monitor and watch the videos to make sure that the subject is moving around as expected.

What is needed is a method and apparatus to provide caregivers a continuous monitoring and risk prediction indicator for the individual health status and activities and thereby avoiding possible deteriorating and life-threatening situations or conditions.

SUMMARY OF THE INVENTION

The present invention includes a method and apparatus to provide one or more indicators for each subject such that the caregivers will be able to provide more individual attention to the health status and possibly avoiding possible health deterioration or life-threatening situations.

As embodied and broadly described herein, an aspect of the present disclosure relates to a method of determining a personalized circadian rhythm identification and prediction from wearable data comprising: obtaining or having obtained data from one or more wearable device(s) during one or more daytime and nighttime cycles; using a processor and a machine learning algorithm comprising: determining a daytime threshold and a nighttime threshold from the data obtained during the one or more daytime and nighttime cycles by: temporally segmenting the data; identifying one or more daytime and nighttime boundary by: selecting from at least one of physical activity, heart rate, or sleep status data; temporally segmenting the physical activity, heart rate, or sleep status data to establish a circadian rhythm; using at least one of a 2-mean, 5-mean, or K-nearest neighbor algorithm to determine the one or more daytime and sleeptime boundaries; and identifying and predicting the personalized circadian rhythm. In one aspect, the method further comprises identifying at least one of: daytime nap times in the daytime data or waking times in the nighttime data. In another aspect, the temporal segments are selected from 0.1, 1, 5, 10, 15, 20, 25, 30, 40, 50, 60, 70, 75, 80, 90, 100 milliseconds, 0.1, 1, 5, 10, 15, 20, 25, 30, 40, 50, 60, 70, 75, 80, 90, 100 seconds, 0.1, 1, 5, 10, 15, 20, 25, 30, 40, 50, 60, 70, 75, 80, 90, to 100 minutes. In another aspect, the temporal segments can be fixed or variable. In another aspect, the sleep status is further defined comprising a setting for awake, asleep, and in bed. In another aspect, the temporal data is further segmented into one or more hyperparameters selected from at least one of start date, duration, sleep time threshold, end data, or one or more intervals. In another aspect, the method further comprises setting one or more sliding windows for any number of consecutive seconds, minutes, hours, days, week, two weeks, months, or years and any other combination or subdivision of these time periods. In another aspect, the method further comprises obtaining temperature and blood pressure data. In another aspect, the method further comprises inferring missing data using a model that predicts trends on the daytime and nighttime boundaries. In another aspect, the daytime and nighttime boundary is determined using a 2-mean algorithm using physical activity and heart rate data. In another aspect, the activity is measured using at least one of: one or more accelerometers (1G, 2G, 3G), measurements in X-, Y-, Z-axis, vectors analysis, one or more gyroscopes, one or more thermometers, once or more pulse-oximeters, one or more oximeters, or combinations thereof. In another aspect, the sleep status data is used to validate the circadian rhythm model using the physical activity and heart rate data. In another aspect, a capability of transmitting the moving window data from microseconds increments to days or weeks or months to the cloud or a networked device containing storage of the raw or timestamped data.

As embodied and broadly described herein, an aspect of the present disclosure relates to a device for determining a personalized circadian rhythm identification and prediction from wearable data comprising: one or more wearable device(s) capable of obtaining or having obtained data from during one or more daytime and nighttime cycles; a processor and a machine learning algorithm that: determines a daytime threshold and a nighttime threshold from the data obtained during the one or more daytime and nighttime cycles by: temporally segmenting the data; identifies one or more daytime and nighttime boundary by: selects from at least one of physical activity, heart rate, or sleep status data;

temporally segments the physical activity, heart rate, or sleep status data to establish a circadian rhythm; uses at least one of a 2-mean, 5-mean, or K-nearest neighbor algorithm to determine the one or more daytime and sleeptime boundaries; and identifies and predicts the personalized circadian rhythm. In one aspect, the processor identifies at least one of: daytime nap times in the daytime data or waking times in the nighttime data. In another aspect, the temporal segments are selected from 0.1, 1, 5, 10, 15, 20, 25, 30, 40, 50, 60, 70, 75, 80, 90, 100 milliseconds, 0.1, 1, 5, 10, 15, 20, 25, 30, 40, 50, 60, 70, 75, 80, 90, 100 seconds, 0.1, 1, 5, 10, 15, 20, 25, 30, 40, 50, 60, 70, 75, 80, 90, to 100 minutes. In another aspect, the temporal segments can be fixed or variable. In another aspect, the sleep status is further defined a comprising a setting for awake, asleep, and in bed. In another aspect, the temporal data is further segmented into one or more hyper-parameters selected from at least one of start date, duration, sleep time threshold, end data, or one or more intervals. In another aspect, the device sets one or more sliding windows for any number of consecutive seconds, minutes, hours, days, week, two weeks, months, or years and any other combination or subdivision of these time periods. In another aspect, the device obtains temperature and blood pressure data. In another aspect, the device infers missing data using a model that predicts trends on the daytime and nighttime boundaries. In another aspect, the device daytime and night-time boundary is determined using a 2-mean algorithm using physical activity and heart rate data. In another aspect, the activity is measured using at least one of: one or more accelerometers (1G, 2G, 3G), measurements in X-, Y-, Z-axis, vectors analysis, one or more gyroscopes, one or more thermometers, once or more pulse-oximeters, one or more oximeters, or combinations thereof. In another aspect, the device sleep status data is used to validate the circadian rhythm model using the physical activity and heart rate data. In another aspect, the device capability of transmitting the moving window data from microseconds increments to days or weeks or months to the cloud or a networked device containing storage of the raw or timestamped data.

As embodied and broadly described herein, an aspect of the present disclosure relates to a non-transitory computer readable medium for providing an ongoing and real time indicator for determining a personalized circadian rhythm identification and prediction from wearable data comprising: obtaining or having obtained data from one or more wearable device(s) during one or more daytime and nighttime cycles; using a processor and a machine learning algorithm comprising: determining a daytime threshold and a night-time threshold from the data obtained during the one or more daytime and nighttime cycles by: temporally segmenting the data; identifying one or more daytime and nighttime boundary by: selecting from at least one of physical activity, heart rate, or sleep status data; temporally segmenting the physical activity, heart rate, or sleep status data to establish a circadian rhythm; using at least one of a 2-mean, 5-mean, or K-nearest neighbor algorithm to determine the one or more daytime and sleeptime boundaries; and identifying and predicting the personalized circadian rhythm.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
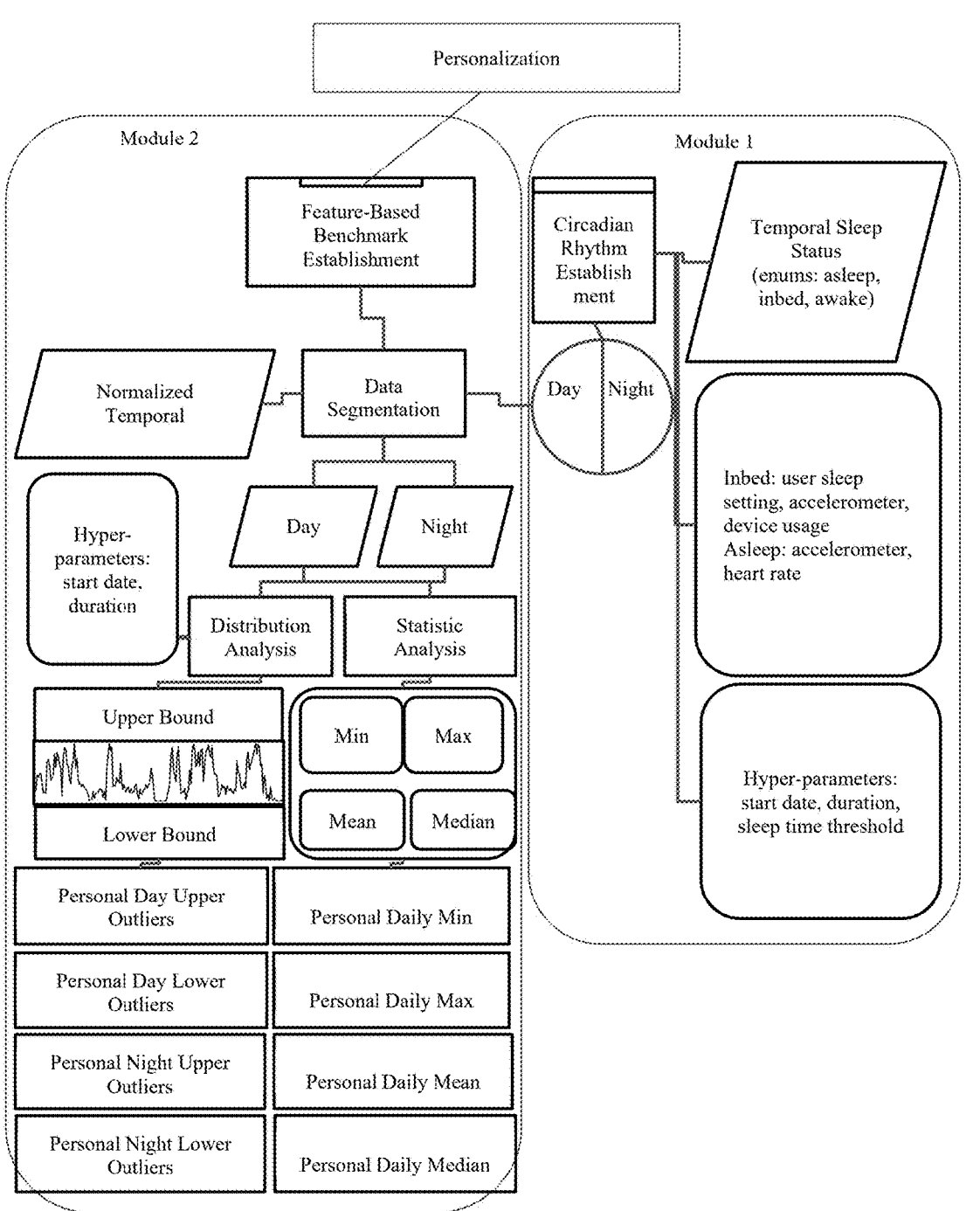
FIG. 1 is a flowchart that shows an overview of the personalized benchmark and health analysis for circadian rhythm, biometrics and physical activities of the present invention. Module 1 (on the right) is for circadian rhythm identification. Module 2 (on the left) is for personalized benchmark establishment and precise risk prediction.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Today, the subject who has endured a medical condition may either enter the hospital or resides in an assisted living home. Both environments are usually served by many healthcare professionals; however these professionals may or may not have the time or energy to provide the individual attention needed to monitor the daily activities of the subject. Today, most healthcare professionals make rounds to each room to ensure that the subject is OK; however, the care giver may or may not see the subject or remember the appropriate activity levels and/or the appropriate daily activity of the subject. Most professionals are too busy to provide organized and regular systematic personal care for each and every subject. As used herein, a major medical event refers to a life-threatening event, or an event that will cause significant, long-term morbidity or mortality, such as a fall that would cause one or more broken bones, significant bruising, damage to soft tissue such as a partial or total lung collapse, concussions, damage to major muscles, heart disease, cardiovascular disease, high blood pressure, and the like.

The present invention includes a method and apparatus to provide an indicator for each subject such that the caregivers will be able to provide more individual attention to the subjects' health status and possibly avoiding possible life-threatening situations. In one example, the subjects are seniors, e.g., having an age greater that 60, 65, 70, 75, 80, 85 or 90 years old. In another example, the subjects are patients in hospital or at home.

The subject is provided a wearable device or set of sensor devices, such as a watch, an exercise band, or health monitoring sensor set. This device may contain accelerometers, blood pressure monitors, thermal monitoring, heart rate, heart rate variability, resting heart rate, sleep status, energy burned, steps, walking/running distance, Bluetooth or Wi-Fi capability, and many other methods to monitor the subject's vitals. However, in this case we have provided a capability to individually monitor and predict risk on a real-time basis using the wearable, the individual activity level or biomarkers which will provide much more information to the healthcare provider.

The method can use three uses a concept of zero movement which can be derived from the incremental counts of 1 gravity (1G), two gravities (2G), 3 gravities (3G), or more. The device can also measure the acceleration(s) in one or more axis, such as X, Y, and/or Z. It is also possible to convolve two or more of the accelerometers to have a directional vector.

Zero movement happens when 1G counts equals 2G counts which equals 3G counts which all equals zero. In other words, zero movement can be defined by the zero summation of counts of 1G, 2G and 3G.

In one embodiment, the present invention includes a device comprising, consisting essentially of, or consisting of: accelerometers for one gravity (1G), two gravity (2G)

and three gravity (3G), or more and/or X, Y, Z-axis, and/or convolving into a vector, measurement capabilities; wherein the accelerometers are capable to monitoring in any continuous time basis from the sub millisecond or microsecond range up to days weeks or months or more; and apply a sliding or moving window from sub seconds to days or weeks or months or more, and to apply calculations to the raw data generated by the accelerometers; having an ability to monitor day, night, activity levels of the subject; and an ability to monitor little to no day, night activity levels of the subject. In another embodiment, the present invention also includes an apparatus for providing an ongoing in real-time indicator for prediction of a use for a lifetime for the person comprising, consisting essentially of, or consisting of: providing an ongoing and real time indicator for predicting remaining lifetimes for one or more subjects comprising: providing a monitoring system connected to the cloud, a Wi-Fi or Bluetooth network which is connected to a wearable device; and providing a wearable device which contains one or more accelerometers, temperature monitoring devices, EKG monitoring devices and other useful devices; wherein the wearable device is powered internally by a battery or other such appropriate energy sources.

In another embodiment, the present invention includes a method for providing an ongoing in real-time indicator to determine a time interval and duration for predicting a change of an active and a resting phase in subjects comprising, consisting essentially of, or consisting of: sampling a time duration of the active and the resting phase of subject recursively for various time intervals of 1 h to Nth hour and time duration of N hour to N+1 hour to obtain active and resting phase data. In another embodiment, the present invention includes a non-transitory computer readable medium for providing an ongoing and real time monitor and risk indicator, comprising instructions stored thereon, that when executed by a computer having a communications interface, one or more databases and one or more processors communicably coupled to the interface and one or more databases, perform the steps comprising, consisting essentially of, or consisting of: providing a monitoring system connected to the cloud, a Wi-Fi or Bluetooth network which is connected to a wearable device; and providing a wearable device which contains one or more accelerometers, temperature monitoring sensors, heart rate monitoring sensors, and other sensors that detect e.g., biometric data, biomarker data, biochemical data, metabolic data, -omics data, etc.; wherein the wearable device is powered internally by a battery or other such appropriate energy sources.

In another embodiment, the present invention includes an apparatus for providing an ongoing and real time indicator comprising, consisting essentially of, or consisting of: a device that samples a time duration of the active and the resting phase of subject recursively for various time intervals of 1 h to Nth hour and time duration of N hour to N+1 hour to obtain an active and resting phase data; a processor comprising a non-transitory computer readable medium connected or connectable to the device to provide an ongoing and real time monitor and risk indicator, comprising instructions stored thereon, that when executed by a computer having a communications interface, one or more databases and one or more processors communicably coupled to the interface and one or more databases.

As used herein, a "higher frequency" of data points refer to data stream that is captured both day and night at least once every second, minute, hour, or day with distinct patterns during day vs. night. This category of data points is continuously measured. Non-limiting examples of higher frequency data stream for use with the present invention include: heart rate, physical activity, active energy burned, basal energy burned, continuous body temperature, continuous cuffless blood pressure. A higher frequency data stream includes data that is obtained every 1 to 60 500 milliseconds, 1 to 60 seconds, 1 to 60 minutes, or 1 to 8 hours.

As used herein, a "medium frequency" of data points refer to a data stream that is captured daily and is conditionally measured, e.g., when subject is resting, when subject is exercising. Non-limiting examples of medium frequency data stream for use with the present invention include a data stream with enough data points to determine from heart rate variability, resting heart rate, step count, walking distance, sleep status, blood oxygen saturation, stress, calories out, respiration, body battery, motion type. A medium frequency data stream includes data that is obtained every 1 to 60 minutes, or 1 to 24 hours 1 to 8 times a day, three times a day, twice a day, or daily.

As used herein, a "low frequency" of data points refers to a data stream with none, or a few data points per day that require manual operation. Non-limiting examples of low frequency data stream for use with the present invention include data streams that are obtained at least weekly selected from manually triggered ECG measure, manually measured blood pressure, manually measured body temperature. A low frequency data stream includes data that is obtained every daily, every other day, three to six times a week, weekly, or monthly.

System 1 is the circadian rhythm identification using the novel circadian ML prediction algorithms. It introduces algorithms and techniques to segment temporal biometric data into distinct day and night segments based on the identified personalized circadian boundaries.

Precision Case Enablement via Personalization: this patent emphasizes personalized health analysis to individual biometric patterns, activating accurate health monitoring and risk prediction solutions.

Extensibility on Use Cases: the system is adaptable to a wide range of wearable data depending on the availability of the biometrics data for a given use case, expanding the system's usability. The data includes, but not limited to, heart rate, heart rate variability, resting heart rate, body temperature, oxygen saturation, blood pressure, physical activities, step count, active energy burned, basal energy burned, and sleep status, etc.

Enhanced Solution Adoption: By addressing outliers such as occasional missing wearable data, the system strengthens the solution adoption.

Architecture Diagram. Following architecture diagram shows an overview of the systems. The workflow starts from module 1 (on the right) for circadian rhythm identification. Then the day/night boundary is streamed to module 2 (on the left) for temporal biometrics data segmentation, personalized benchmark establishment, and precise health condition analysis and risk prediction.

FIG. 1. Personalized benchmark and health analysis for circadian rhythm, biometrics and physical activities. Module 1 (on the right) is for circadian rhythm identification. Module 2 (on the left) is for personalized benchmark establishment and precise risk prediction.

System 1: Circadian Rhythm Machine Learning (ML) Prediction.

Motivation. To achieve the risk prediction accuracy, the inventors segmented the wearable temporal biometric features into day and night segments because they exhibit different thresholds and patterns. Besides the daily based data segmentation, the long-term trend of the day and night boundary for a given subject, nap in day time, activities at night time are important signals to risk prediction AI models.

There are sleep tracking products on the market. However, most of the algorithms are proprietary and the underlying raw data based on which the algorithms were developed is not publicly accessible. Instead of asking platform users to purchase and wear another commercially available device to track sleep, the inventors developed a circadian algorithm using the same wearable that is used to predict risk, however, the present invention can use any data platform/wearable device as a source of data. By being agnostic as to the data platform/wearable device, the approach of the present invention reduces both the cost and complexity for the subjects.

The method of actigraphy to estimate sleep only relies on movement data and is not able to detect certain wake moments at night. To overcome this issue, the inventors developed multi-dimensional biometric feature algorithms to detect circadian rhythm.

Dataset. The present invention used acceleration (in g-force unit: 9.8 m/s2), heart rate (bpm), and sleep status from wearable devices to identify circadian rhythm. The AI model is extensible to incorporate other biometric features, such as temperature, blood pressure.

Specific to the experimentation result mentioned in this patent, the data was collected using each data entry is associated with a unique code per subject. The personal identifiable information is not present in the dataset. Typical frequency of the data features is shown below. It depends on the sensor devices and subjects' movement status, etc. The average data frequency of the acceleration data is around 1 data point/minute. When the subject is in exercise, the frequency increases up to a few hundred milliseconds. The average data frequency of the heart rate data in general is 3-7 minutes. It's also observed at higher frequencies, such as in a few seconds.

TABLE 1

| Sample heart rate wearable data in raw data format | |
|---|---|
| createLocalTime | heartRate |
| 09:14:00.393 | 64 |
| 09:19:23.518 | 65 |
| 09:22:04.518 | 64 |
| 09:28:13.520 | 58 |
| 09:35:03.526 | 64 |
| 09:37:26.526 | 66 |
| 09:41:50.521 | 69 |
| 09:47:53.770 | 87 |
| 09:56:19.769 | 96 |
| 10:01:23.769 | 87 |
| 10:06:31.769 | 71 |
| 10:10:06.771 | 72 |
| . . . | . . . |
| 10:31:42.646 | 136 |
| 10:31:50.646 | 136 |
| 10:31:51.646 | 136 |
| 10:32:00.646 | 137 |
| 10:32:03.646 | 138 |
| 10:32:06.646 | 139 |
| 10:32:15.646 | 141 |
| 10:32:20.646 | 141 |
| 10:32:22.646 | 140 |
| 10:32:28.646 | 141 |
| 10:32:33.646 | 141 |
| 10:32:39.646 | 139 |

Wearable device detects and sends sleep status in categorical values: asleep, inBed, awake.

InBed: wearable device considers user sleep setting, accelerometer, device usage.

Asleep: wearable device considers accelerometer, heart rate.

TABLE 2

| Sample sleep analysis wearable data in raw data format from Wearable device. | |
| --- | --- |
| createLocalTime | sleepAnalysis |
| 2023-04-19 00:44:58 | asleep |
| 2023-04-19 00:57:58 | asleep |
| 2023-04-19 01:09:28 | asleep |
| 2023-04-19 01:18:58 | asleep |
| 2023-04-19 01:34:28 | asleep |
| . . . | . . . |
| 2023-04-21 07:49:44 | awake |
| 2023-04-21 07:51:14 | inBed |
| 2023-04-21 07:53:14 | awake |
| 2023-04-21 07:54:44 | inBed |
| 2023-04-21 07:56:04 | inBed |

Data Availability Compliance. The subjects are required to wear the devices 75% of the time per day (with 6 hours for charging and some buffer time), and 4 days of the week (minimum 3 workdays and 1 weekend). The daily wear should cover both day and night time.

Data Preprocessing and Normalization.

First, remove the following disqualified subjects, e.g., that that violate one or more of the following: those who violate the data availability compliance, those who experiment less than the benchmark period (e.g., 10 days), those who travel to another time zone during personalized benchmark establishment time, and/or more than 10% of the total experimentation time.

Then, the acceleration data and heart rate data are normalized to a consistent interval (e.g., 1, 300, 600, 3,600 seconds depending on the use cases). The 3-dimensional acceleration data (x, y, z-axis) is normalized to 1 dimension, and/or 1G, 2G, 3G, or more, and/or convolving into one or more vector(s).

Circadian Machine Learning (ML) Prediction Algorithms.

The inventors developed the approach described below. The following illustration is based on three input features: acceleration, heart rate and sleep status. The AI model framework is extensible to incorporate other biometric features, such as temperature, blood pressure.

For approach 1 and 2 are where the system does not receive sleep status from the subject wearable device, the system then uses available biometrics data to infer circadian rhythm. To validate the model performance, the inventors used sleep status as labels to cross check the circadian rhythm model accuracy.

For approach 3 the system gets biometrics data as well as sleep status data from the subject wearable device, the inventors used both biometrics data and sleep status data as input features for model development to enhance the accuracy.

Approach 1—Acceleration-Based Analysis.

Data Plot. The following figures show physical activities for a sample subject for a full day. The physical activity measures are used as the input feature to training the ML model. The inventors used sleep status from a wearable device as a benchmark label to evaluate the model accuracy. Sleep status labels are categorical values. The inventors used the categorical values "asleep" and "inbed" as training labels.

Figure 2:
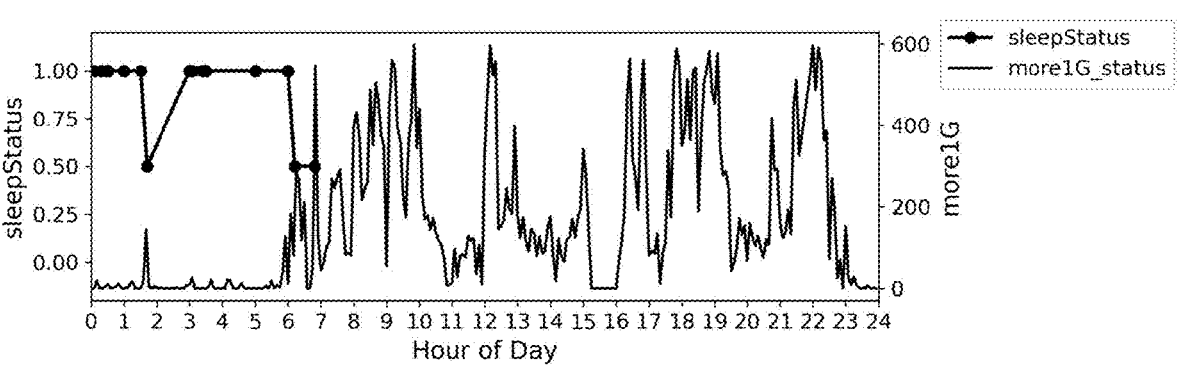
FIG. 2 is a graph that shows a sample subject's physical activities for a full day. X-axis shows the 0-24 hour of a day. For the Y-axis, scale on the right shows the physical activities, and scale on the left shows the sleep status as labels. When the subject moved at night, the sleep status transitioned from asleep (1.0) to inbed (0.5). This transition correlates with the physical activities peaks.

FIG. 2 is a graph that shows the sample subject's physical activities for a full day. X-axis shows the 0-24 hour of a day. For the Y-axis, scale on the right shows the physical activities, and scale on the left shows the sleep status as labels. When the subject moved at night, the sleep status transitioned from asleep (1.0) to inbed (0.5). This transition correlates with the physical activities peaks.

Figure 3:
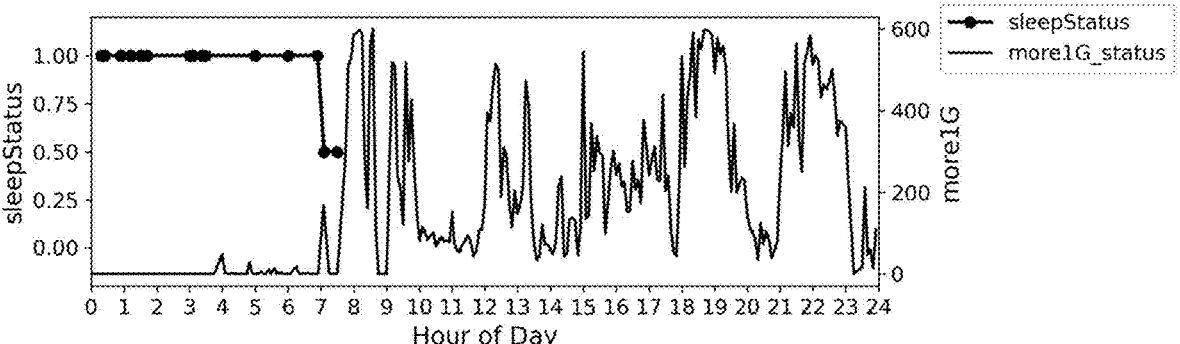
FIG. 3 is a graph that shows another sample subject's physical activities for a full day.

FIG. 3 is a graph that shows another sample subject's physical activities for a full day.

Intuition of Physical Activities Correlation with Sleep Labels. The inventors calculated the physical activities' hourly mean, hourly max and hourly min. In order to get intuition and visually observe the correlation between physical activities statistic values with the sleep labels, the inventors plotted the data in one graph.

First, the inventors plotted the hourly mean, and color-coded the values with labels (sleep time in blue and non-sleep time in orange).

Figure 4:
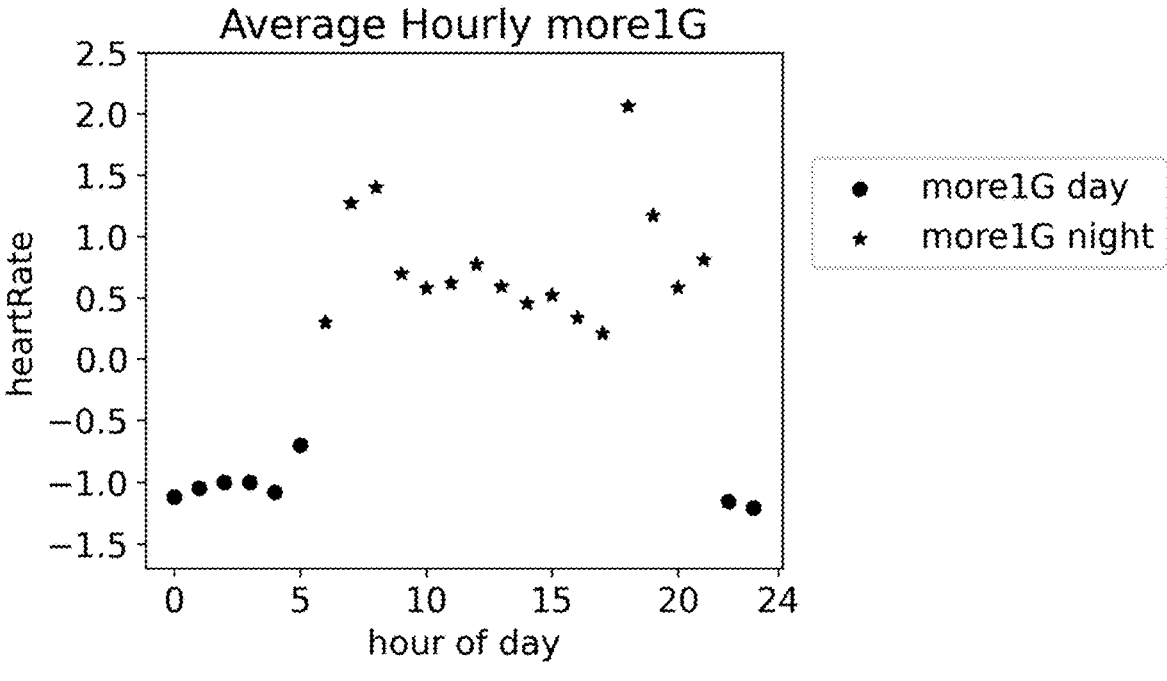
FIG. 4 is a graph that shows a plot of physical activities hourly mean (y-axis) along 24 hours for a given day (x-axis). The y-axis value is normalized between [−1, 1].

FIG. 4 is a graph that shows physical activities hourly mean (y-axis) along 24 hours for a given day (x-axis). The sleep labels are color coded with sleep time in blue and non-sleep time in orange. This graph visualizes the correlation between physical activities hourly mean and sleep labels.

Then, the inventors plotted the hourly min and max, and color-coded the values with labels (sleep time in blue and non-sleep time in orange).

Figure 5:
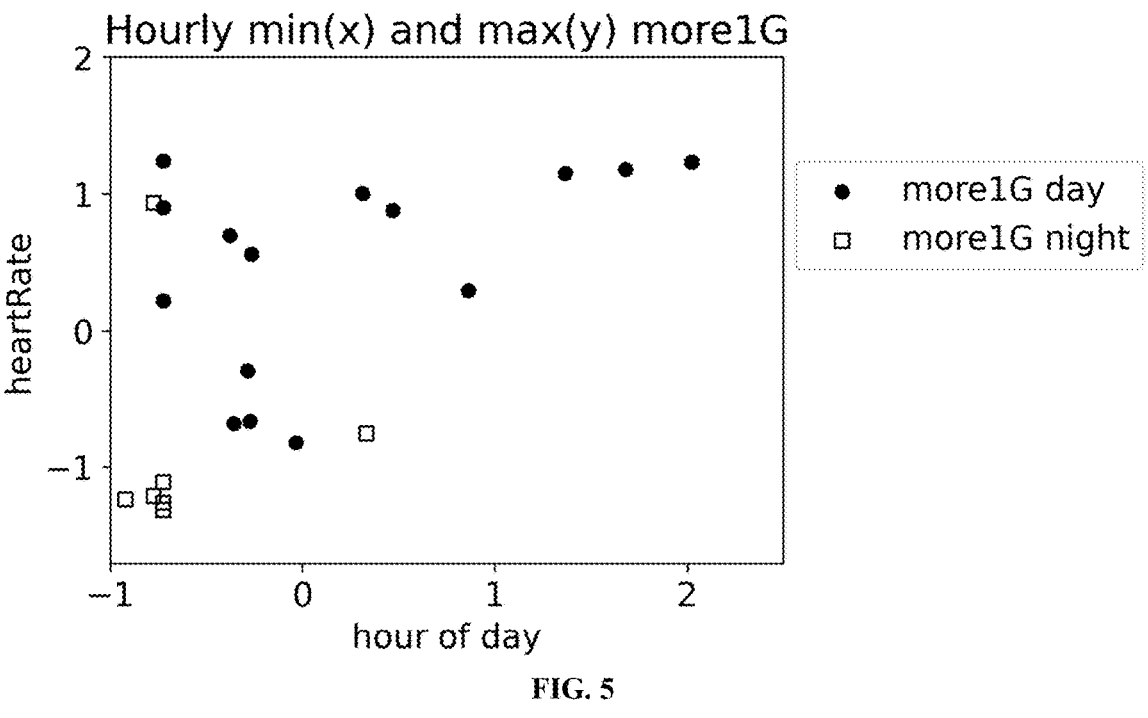
FIG. 5 is a graph that shows a plot of physical activities hourly min (x-axis) and hourly max (y-axis).

FIG. 5 is a graph that shows physical activities hourly min (x-axis) and hourly max (y-axis). The sleep labels are color coded with sleep time in blue and non-sleep time in orange. This graph visualizes the correlation between \hourly min/max and sleep labels.

Based on computation, the hourly mean of physical activities show stronger correlation with sleep status.

Approach 2—Acceleration and Heart Rate-Based Analysis.

Data Plot. The following figures show physical activities and heart rate for a sample subject for a full day. The heart rate measures are used as the input feature to training the ML model. The inventors used sleep status from Wearable device as a benchmark label to evaluate the model accuracy. Sleep status labels are categorical values. The inventors used the categorical values "asleep" and "inbed" as training labels.

Figure 6:
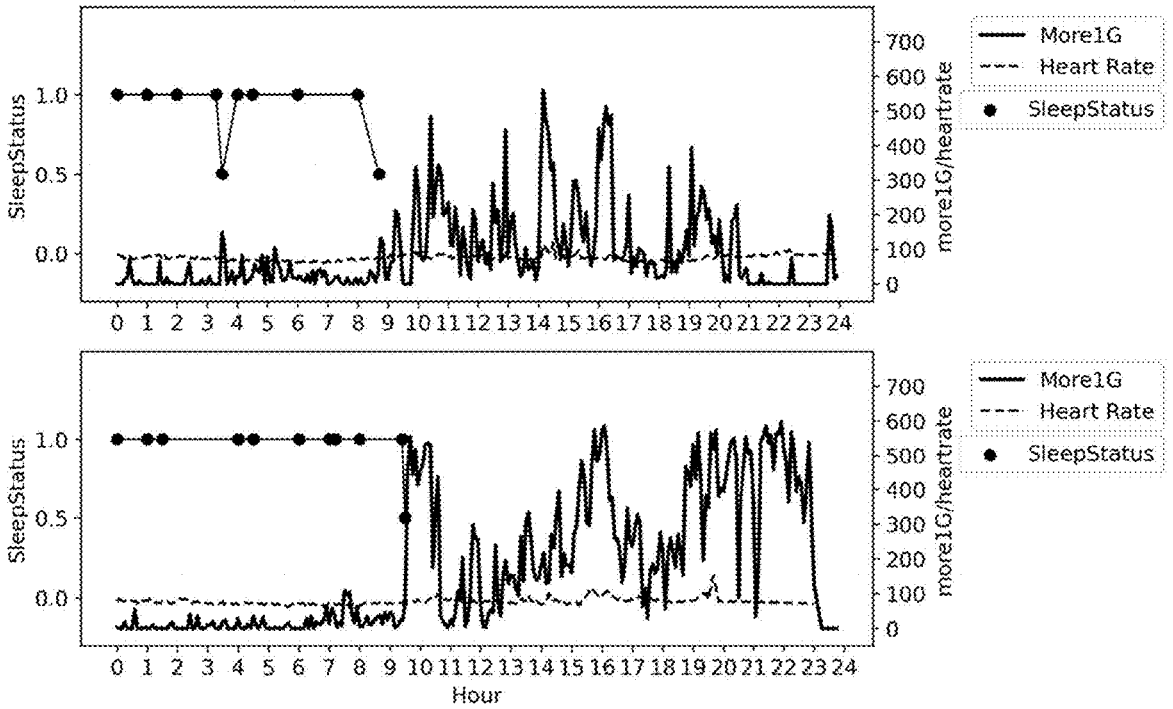
FIG. 6 are graphs that shows a sample subject's physical activities and heart rate for a full day. X-axis shows the 0-24 hour of a day. For the Y-axis, scale on the right shows the physical activities, and scale on the left shows the sleep status as labels. This figure visualizes physical activities (curve lines in red) and heart rate (curve lines in blue) trends between the day and night periods.

FIG. 6 are graphs that shows a sample subject's physical activities and heart rate for a full day. X-axis shows the 0-24 hour of a day. For the Y-axis, scale on the right shows the heart rate, and scale on the left shows the sleep status as labels. This figure visualizes physical activities and heart rate trends between the day and night periods.

Intuition of Physical Activities and Heart Rate Correlation with Sleep Labels.

First, the inventors calculated the heart rate' hourly mean and plotted the data in the graph.

Figure 7:
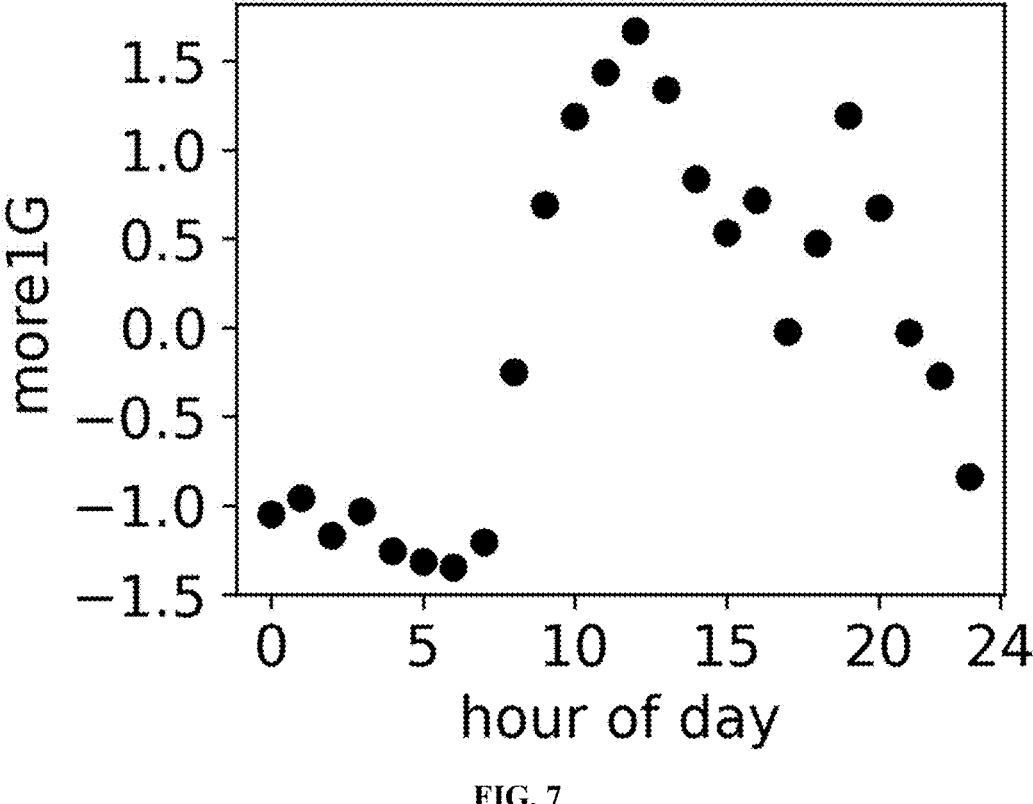
FIG. 7 is a graph that shows a plot of heart rate normalized hourly mean (y-axis) along 24 hours for a given day (x-axis).

FIG. 7 is a graph that shows heart rate hourly mean (y-axis) along 24 hours for a given day (x-axis).

Then, the inventors plotted the hourly mean of both physical activities and heart rate, and color-coded the values with labels (sleep time in blue and non-sleep time in orange).

Figure 8:
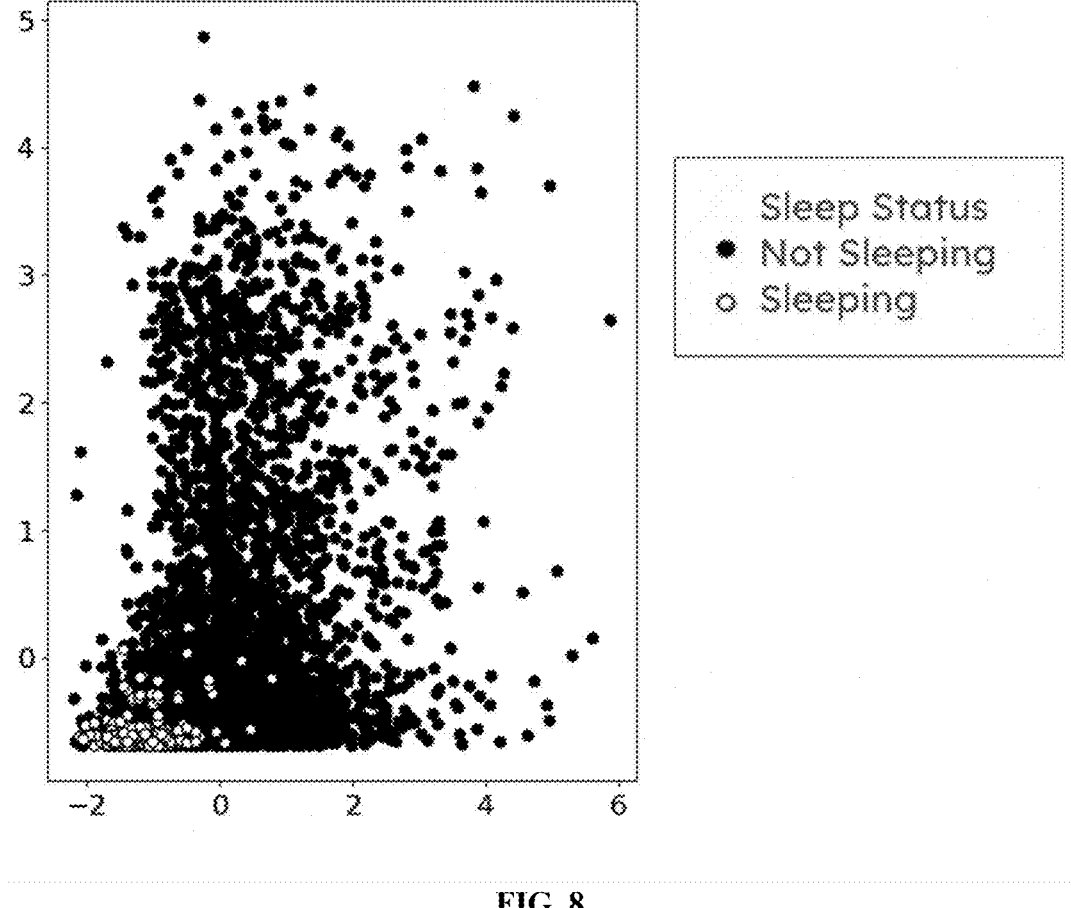
FIG. 8 is a graph that shows a plot of heart rate normalized hourly mean (x-axis) and physical activities normalized hourly mean (y-axis).

FIG. 8 is a graph that shows heart rate hourly mean (x-axis) and physical activities hourly mean (y-axis). The sleep labels are color coded with sleep time in blue and non-sleep time in orange. This graph visualizes the correlation between the hourly mean of physical activities, heart rate and sleep labels.

Approach 3—Acceleration, Heart Rate, and Sleep Status-Based Analysis

If subjects provide sleep status as part of the wearable data, the system adjusts to approach 3, which uses sleep status as part of the input feature to enhance the accuracy. ML Prediction Results Analysis.

The inventors experimented and tuned different algorithms: 2-Mean, 5-Means clustering on one feature, on multiple features, and K-Nearest Neighbors. One example of a selection is K-Mean on hourly mean values.

Following graphs illustrate 2-Mean, 5-Means and K-Nearest Neighbors.

Figure 9:
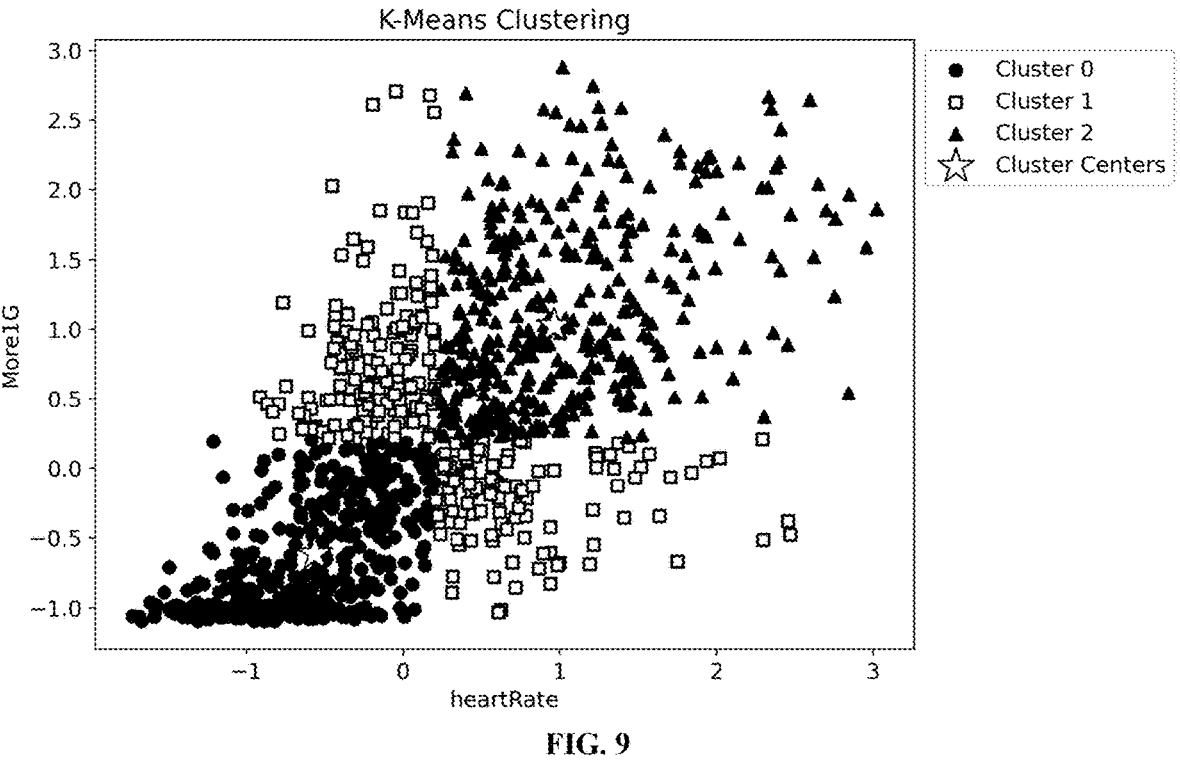
FIG. 9 is a graph that shows a Joined 2-Mean on multiple features. X-axis represents heart rate, y-axis represents physical activities. Color represents predicted clusters.

FIG. 9 is a graph that shows Joined 2-Mean on multiple features. X-axis represents heart rate, y-axis represents physical activities. Color represents predicted clusters.

Figure 10:
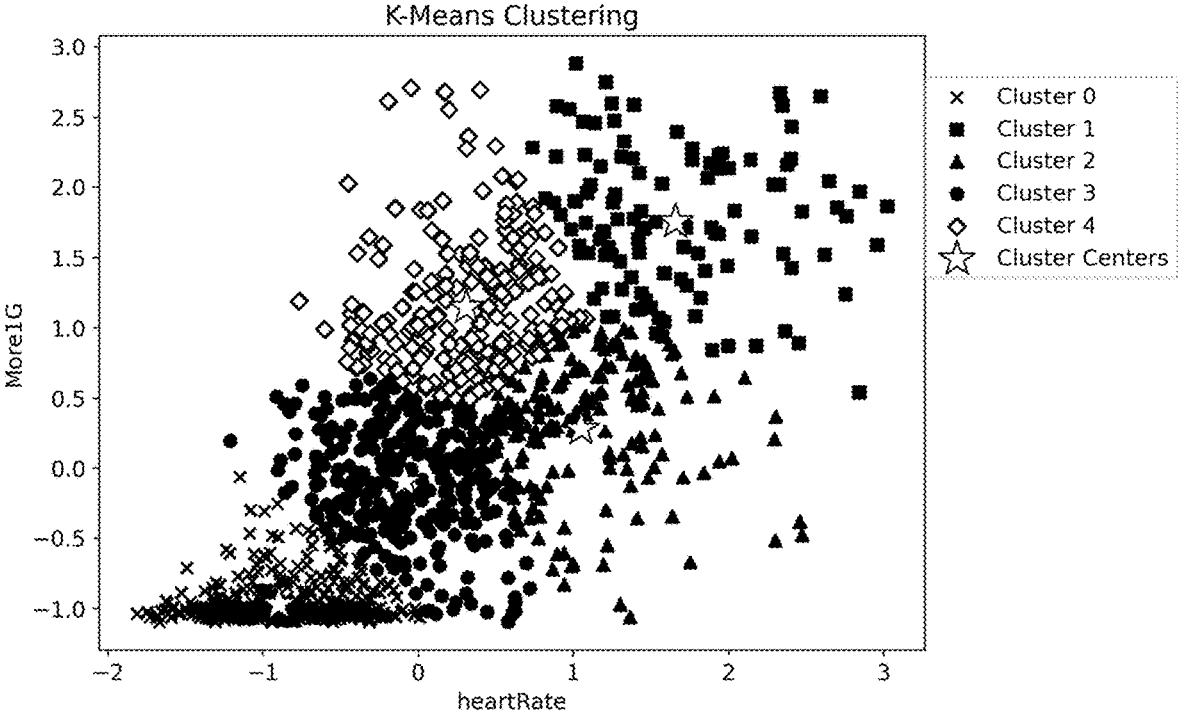
FIG. 10 is a graph that shows a 5-Mean on multiple features. X-axis represents physical activities, y-axis represents heart rate. Color represents predicted clusters.

FIG. 10 is a graph that shows 5-Mean on multiple features. X-axis represents physical activities, y-axis represents heart rate. Color represents predicted clusters.

Figure 11:
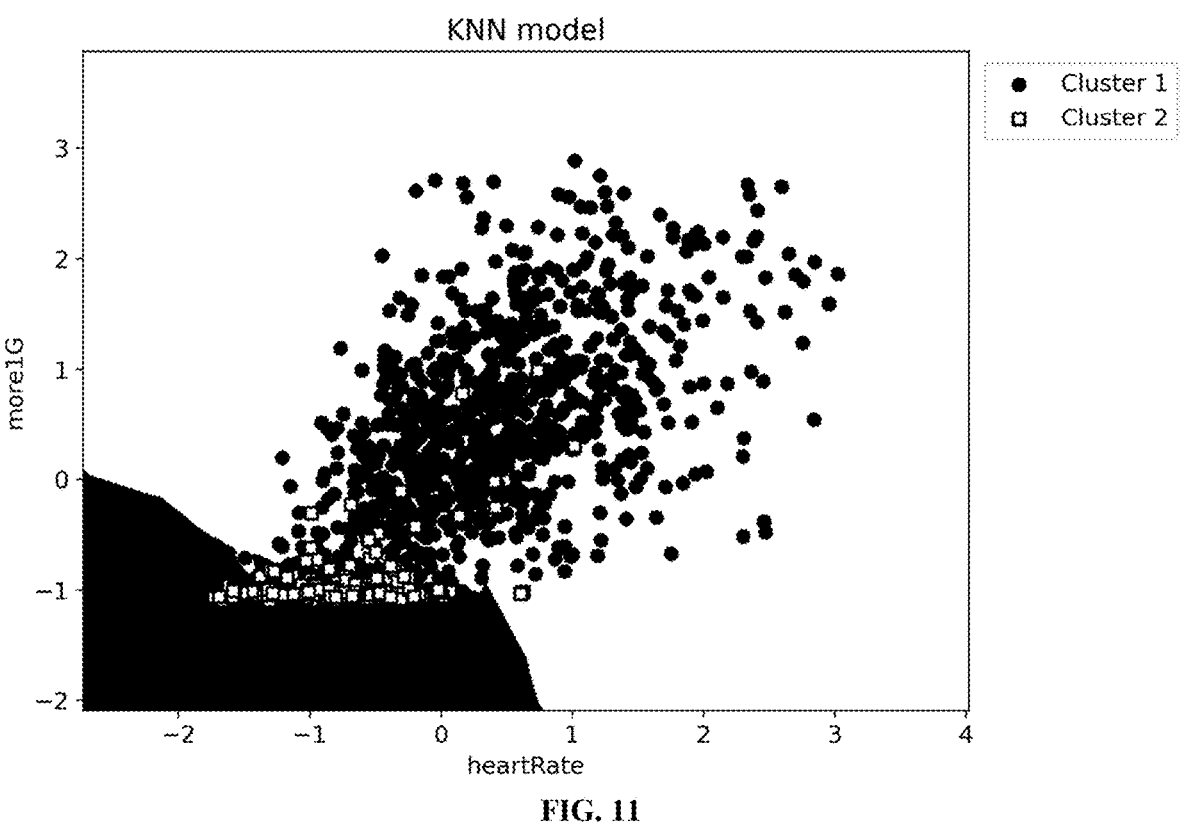
FIG. 11 is a graph that shows a K-Nearest Neighbors experimentation. X-axis represents heart rate, y-axis represents physical activities. Color represents prediction results on sleep vs. non-sleep time.

FIG. 11 is a graph that shows K-Nearest Neighbors experimentation. X-axis represents heart rate, y-axis represents physical activities. Color represents prediction results on sleep vs. non-sleep time.

Figure 12:
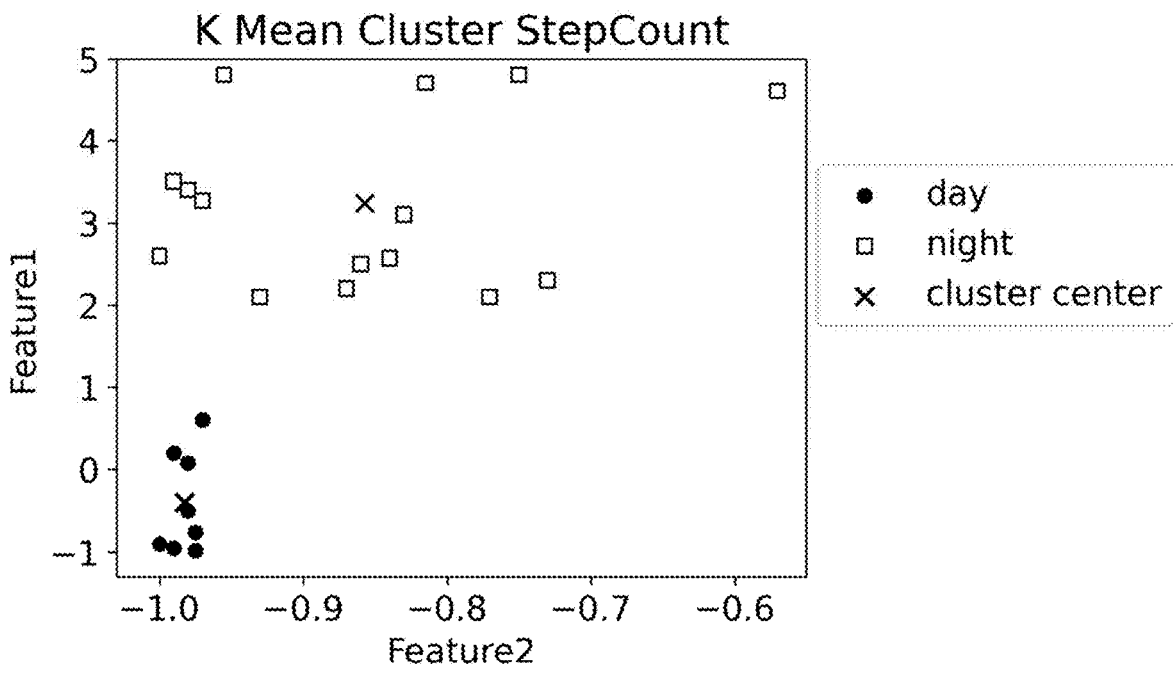
FIG. 12 is a graph that shows a K-Mean analysis. X-axis represents heart rate, and y-axis represents physical activities. Color represents prediction results on sleep (yellow) vs. non-sleep time (purple).

FIG. 12 is a graph that shows K-Mean analysis. X-axis represents heart rate, and y-axis represents physical activities. Color represents prediction results on sleep (yellow) vs. non-sleep time (purple).

The best selection algorithm for this data was shown to be the 2-Mean on hourly mean of Heart Rate and Physical Activities.

TABLE 3

| Circadian ML Model Precision Result. | | | |
| --- | --- | --- | --- |
| | 2-Mean on Heart Rate and Physical Activities | Joined 2-Mean on Heart Rate and Physical Activities | 5-Mean on Heart Rate and Physical Activities |
| Accuracy | 0.9167 | 0.7822 | 0.4768 |
| Precision | 0.7778 | 0.5339 | 0.9728 |
| Sensitivity/Recall | 1.0000 | 0.9921 | 0.3118 |
| Specificity | 0.8824 | 0.7125 | 0.9738 |

Handle the Outliers.

Outlier Scenarios. Occasional missing data points, e.g., missing data at night.

Figure 13:
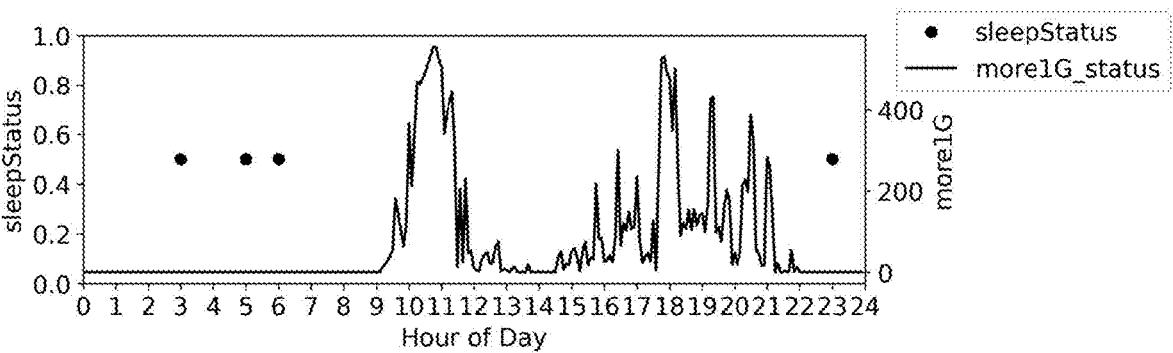
FIG. 13 is a graph that shows a sample sleep analysis when subject did not wear wearable device at night.

FIG. 13 is a graph that shows sample sleep analysis when subject did not wear Wearable device at night.

Wearable device runs out of battery or in charging.

Figure 14:
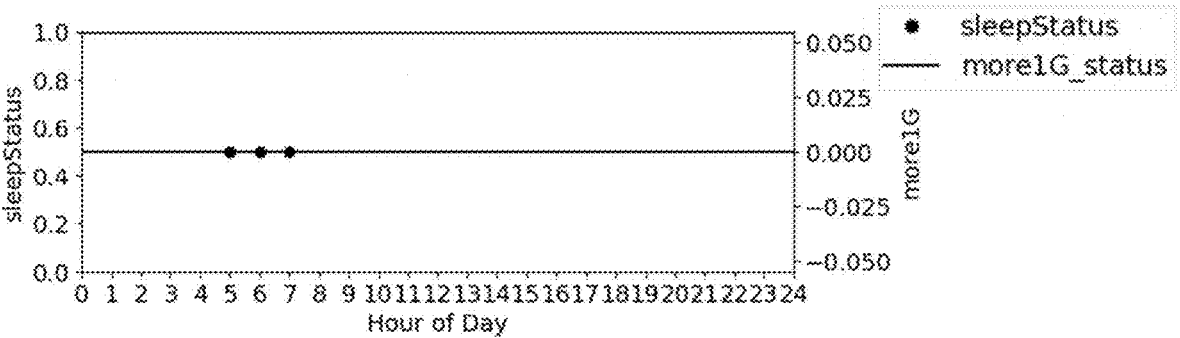
FIG. 14 is a graph that shows a sample sleep analysis when subject did not wear wearable device for the full day. The sleep status is based on the sleep configuration in the health app.

FIG. 14 is a graph that shows sample sleep analysis when the wearable device is not in use for the whole day. Therefore, the inventors only observed inBed status without asleep and awake. This diagram further proves that the inBed status is dependent on phone setting.

Subjects take nap(s) during the daytime, the inventors have observed this especially in subjects and senior subjects. In a trial, the inventors observed daytime sleep status for fatigue subjects.

Solutions to Handle the Outliers.

The inventors defined the following hyper-parameters to address the above-mentioned outliers in order to enhance the analysis accuracy and solution adoption:

Define the time window to generate the personal benchmark. This period of days is configured as hyper-parameters. By default, the system sets it to 10 days, but it can be adjusted as needed.

Aggregate across a period of days to account for the missing data points for a few days in between. This was to address outliers scenario 1 (occasional missing data) and scenario 2 (run out of battery). Below is one example of a possible scenario.

Benchmark start date, e.g., start of the clinical trial.

Benchmark duration, e.g., 10 days.

Variable depending on the disease types, ranging from 1 day to 30 days.

E.g., heart failure recovering subjects/long-COVID subjects: 10 days.

E.g., knee replacement subjects: 15 days.

E.g., chronicle disease: 30 days.

Set sleep time threshold to address outlier scenario 3 (nap) mentioned above.

Use rolling mean algorithm to differentiate sleep vs. short time nap.

If the input features do not have sleep analysis, the system can use physical activities and heart rate information to infer the circadian rhythm. Day/Night Boundary Results.

Based on the above algorithms, the inventors derived the personalized day and night boundary as circadian rhythm. Here are some examples of the established benchmark results.

TABLE 4

| Computed circadian rhythm for sample subjects. The values presented in the table are time of the day. | | |
| --- | --- | --- |
| Patient ID | Wake | Sleep |
| | 6.78 | 24 |
| | 6.69 | 22.11 |
| | 7.42 | 24 |
| | 10.83 | 20.4 |
| | 5.29 | 23 |
| | 7.64 | 22.73 |

Figure 15:
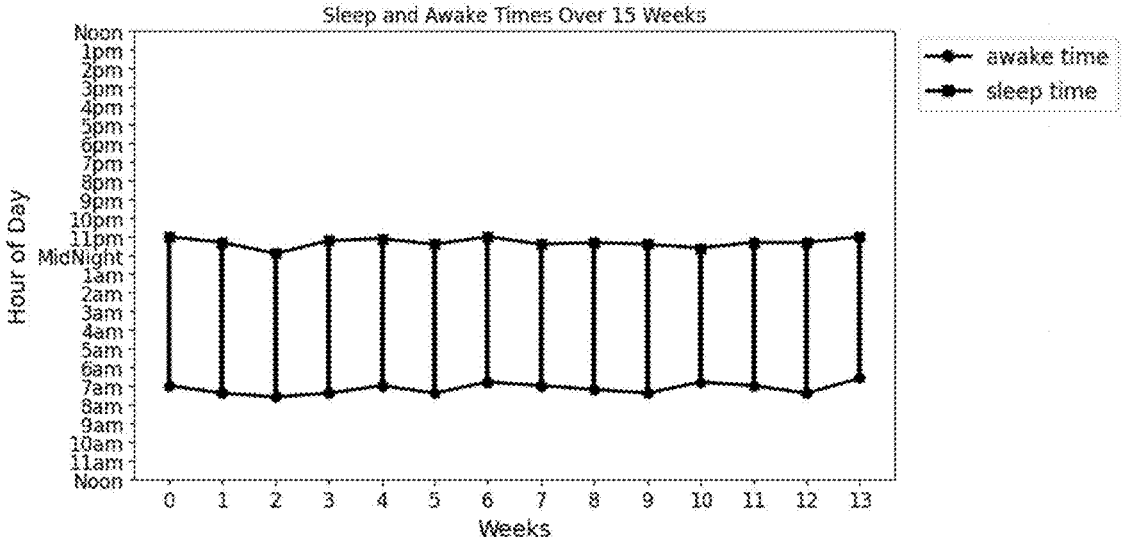
FIG. 15 is a graph that shows a sleep pattern week-over-week changes for subject 1.

Following two diagrams demonstrate the trend of the personalized circadian rhythm. FIG. 15 is a graph that shows sleep pattern week-over-week changes for subject 1.

Figures 16, 17:
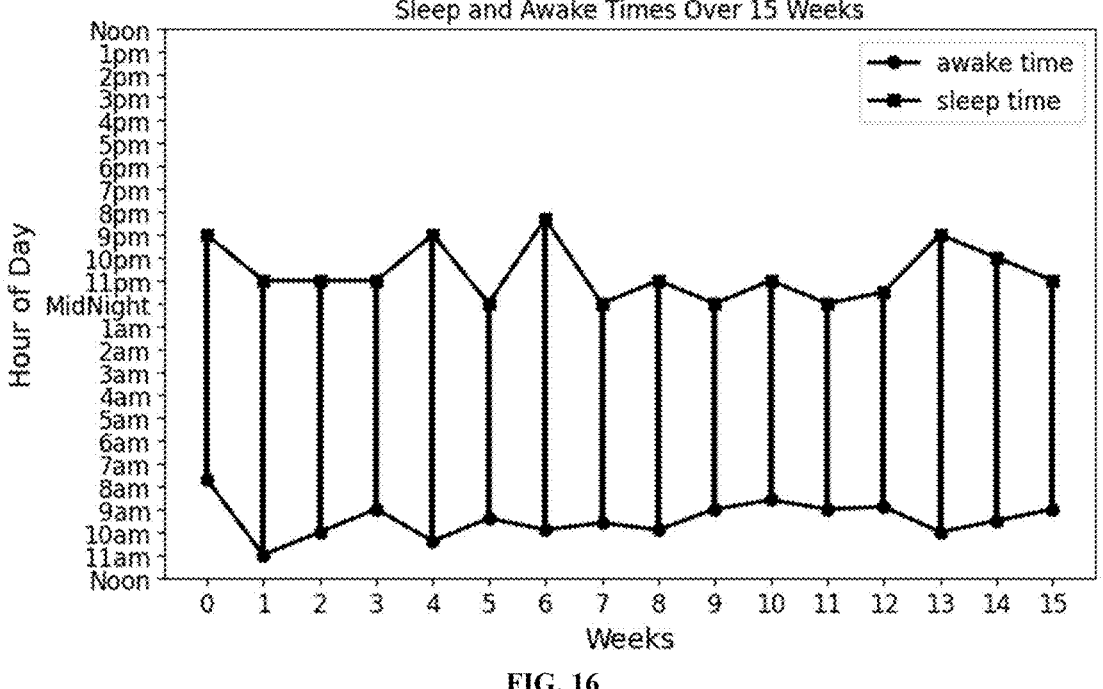
FIG. 16 is a graph that shows a sleep pattern week-over-week changes for subject 2.
FIG. 17 is a graph that shows illustrates the asleep and awake distribution across subjects population. It is based on weekly aggregation. It tolerates missing data entries for a few days.

FIG. 16 is a graph that shows sleep pattern week-over-week changes for subject 2.

FIG. 17 is a graph that shows the asleep and awake distribution across subjects population. It is based on weekly aggregation. It tolerates missing data entries for a few days.

The output from system 1 is served as input to system 2: circadian rhythm (day/night boundary) so that the system can segment the temporal data into day segment and night segment. In system 2, the system will conduct personalized distribution analysis and statistical analysis.

Clinical utility. Determining the circadian rhythm of a subject is required to place in context one or more inputs from one or more sensor devices over time for the subject. Initially, it is necessary to provide baseline data for the subject, but after determining the baseline, it is necessary to know where in their circadian rhythm sensor data is captured to evaluate whether, e.g., a sudden increase in heart rate, blood pressure, temperature, etc., is detected while the subject is awake or asleep. A clinical correlation is then possible depending on the portion of the circadian rhythm in which the biometric data is measured. For example, having determined the baseline data for the subject, e.g., when they wake up and there is an increase in heart rate, blood pressure, etc., it is possible to determine if there is an event that occurs during the day is the result of a clinical disease or disorder, or if the subject is merely waking up from a nap. It is also possible to know the effect of, e.g., taking a drug and measuring any immediate or long-term effects of taking the drug, e.g., changes in heart rate, QT prolongation, sudden changes in blood pressure or temperature, etc. Non-limiting examples of biometric data include, e.g., heart rate, physical activity, active energy burned, basal energy burned, continuous body temperature, continuous cuffed or cuffless blood pressure.

The circadian rhythm can also be used to detect abnormal diurnal change of heart rate. The day heart rate is, on average, higher than the night heart rate. For certain patients, reversed measures are observed which is an alarming signal.

Precision care based on segmented personalized benchmark. The circadian rhythm can also be used to establish daytime-personalized benchmarks and nighttime-personalized benchmarks for each subject based on which the outliers are captured and processed by machine learning for alarm detection. By having one or more benchmarks through 24 hrs period(s), the upper and lower range can be varied to improve the detection of anomalies for determining when to provide an alarm signal.

Evolvement of the circadian rhythm. The circadian rhythm is generally a relatively stable measure. However, using the present invention it is possible to detect anomalies in the data with just one week of data or less. Using the present invention, one or two special events will not make a significant impact on the circadian rhythm. However, the present inventors have observed that while subjects are recovering, they have improved circadian rhythm: longer uninterrupted sleep, more consistent sleep and awake time, etc. As such, it is now possible to use circadian rhythm change, though relatively stable, as a sign of recovery.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A method of determining a personalized circadian rhythm identification and prediction from wearable data obtained from one or more wearable device(s) of a patient comprising:

obtaining or having obtained data from the one or more wearable device(s) during one or more daytime and nighttime cycles;

using a processor and a machine learning algorithm comprising:

using an XGBoost algorithm modified for categorical analysis by splitting data into trees using a pre-computed number of categories based on first axis, second axis, and third axis measurements, which trees also include independent dummy variables to eliminate when no data is available, wherein the modified XGBoost algorithm generates a predicted trajectory of resting and active phase of when there will be little to no day, or night activity levels of the patient;

determining a daytime threshold and a nighttime threshold from the data obtained during the one or more daytime and nighttime cycles by:

identifying one or more daytime and nighttime boundaries by:

selecting from at least one of physical activity, heart rate, or sleep status data;

temporally segmenting the physical activity, heart rate, or sleep status data to establish a circadian rhythm;

using at least one of a 2-mean, 5-mean, or K-nearest neighbor algorithm to determine the one or more daytime and nighttime boundaries; and identifying and predicting the personalized circadian rhythm.

2. The method of claim 1, further comprising identifying at least one of: daytime nap times in daytime data or waking times in nighttime data.

3. The method of claim 1, wherein the temporal segments for the at least one of physical activity, heart rate, or sleep status are selected from 0.1, 1, 5, 10, 15, 20, 25, 30, 40, 50, 60, 70, 75, 80, 90, 100 milliseconds, 1, 5, 10, 15, 20, 25, 30, 40, 50, 60, 70, 75, 80, 90, 100 seconds, 1, 5, 10, 15, 20, 25, 30, 40, 50, 60, 70, 75, 80, 90, to 100 minutes.

4. The method of claim 1, wherein the temporal segments for the at least one of physical activity, heart rate, or sleep status can be fixed or variable.

5. The method of claim 1, further comprising obtaining temporal data which is raw or timestamped data and is further marked into one or more hyperparameters selected from at least one of start date, duration, sleep time threshold, end data, or one or more intervals.

6. The method of claim 5, further comprising transmitting the one or more sliding windows to a global telecommunications network or a networked device containing storage of the raw or timestamped data.

7. The method of claim 1, further comprising setting one or more sliding windows for any number of consecutive seconds, minutes, hours, days, week, two weeks, months, or years and any other combination or subdivision of these time periods.

8. The method of claim 1, further comprising inferring missing data using a circadian rhythm model from data obtained from the user to predict trends on the one or more daytime and nighttime boundaries.

9. The method of claim 1, further comprising obtaining the physical activity and the heart rate data, wherein the one or more daytime and nighttime boundaries are determined using the 2-mean algorithm of the physical activity and the heart rate data.

10. The method of claim 1, further comprising obtaining the physical activity data using at least one of: one or more accelerometers (one gravity (1G), two gravities (2G), three gravities (3G)), measurements in X-, Y-, Z-axis, vectors analysis, one or more gyroscopes, one or more thermometers, once or more pulse-oximeters, one or more oximeters, or combinations thereof.

11. The method of claim 1, wherein the sleep status data is used to validate a circadian rhythm model.

12. A device for determining a personalized circadian rhythm identification and prediction of a patient comprising:

one or more wearable device(s) capable of obtaining or having obtained data from during one or more daytime and nighttime cycles;

a processor and a machine learning algorithm that:

uses an XGBoost algorithm modified for categorical analysis by splitting data into trees using a pre-computed number of categories based on first axis, second axis, and third axis measurements, which trees also include independent dummy variables to eliminate when no data is available, wherein the modified XGBoost algorithm generates a predicted trajectory of resting and active phase of when there will be little to no day, or night activity levels of the patient;

determines a daytime threshold and a nighttime threshold from the data obtained during the one or more daytime and nighttime cycles by:

identifying one or more daytime and nighttime boundaries by:

selecting from at least one of physical activity, heart rate, or sleep status data;

temporally segmenting the physical activity, heart rate, or sleep status data to establish a circadian rhythm;

using at least one of a 2-mean, 5-mean, or K-nearest neighbor algorithm to determine the one or more daytime and nighttime boundaries; and using the processor to identify the personalized circadian rhythm.

13. The device of claim 12, wherein the processor identifies at least one of: daytime nap times in daytime data or waking times in nighttime data.

14. The device of claim 12, wherein the temporal segments for the at least one of physical activity, heart rate, or sleep status are selected from 0.1, 1, 5, 10, 15, 20, 25, 30, 40, 50, 60, 70, 75, 80, 90, 100 milliseconds, 1, 5, 10, 15, 20, 25, 30, 40, 50, 60, 70, 75, 80, 90, 100 seconds, 1, 5, 10, 15, 20, 25, 30, 40, 50, 60, 70, 75, 80, 90, to 100 minutes.

15. The device of claim 12, wherein the temporal segments for the at least one of physical activity, heart rate, or sleep status can be fixed or variable.

16. The device of claim 12, wherein the temporal data which is raw or timestamped data and is further marked into one or more hyperparameters selected from at least one of start date, duration, sleep time threshold, end data, or one or more intervals.

17. The device of claim 16, further comprising transmitting the one or more sliding windows to a global telecommunications network or a networked device containing storage of the raw or timestamped data.

18. The device of claim 12, the device sets one or more sliding windows for any number of consecutive seconds, minutes, hours, days, week, two weeks, months, or years and any other combination or subdivision of these time periods.

19. The device of claim 12, the device infers missing data using a circadian rhythm model from data obtained from the user to predict trends of the one or more daytime and nighttime boundaries.

20. The device of claim 12, further comprising obtaining the physical activity and the heart rate data, wherein the one or more daytime and nighttime boundaries are determined using a 2-mean algorithm of the physical activity and the heart rate data.

21. The device of claim 12, further comprising obtaining the physical activity data using at least one of: one or more accelerometers (one gravity (1G), two gravities (2G), three gravities (3G)), measurements in X-, Y-, Z-axis, vectors analysis, one or more gyroscopes, one or more thermometers, once or more pulse-oximeters, one or more oximeters, or combinations thereof.

22. The device of claim 12, wherein the sleep status data is used to validate a circadian rhythm model.

23. A non-transitory computer readable medium for providing an ongoing and real time indicator for determining a personalized circadian rhythm identification and prediction from wearable data obtained from one or more wearable device(s) comprising:

obtaining or having obtained data from the one or more wearable device(s) during one or more daytime and nighttime cycles;

using a processor and a machine learning algorithm comprising:

using an XGBoost algorithm modified for categorical analysis by splitting data into trees using a pre-computed number of categories based on first axis, second axis, and third axis measurements, which trees also include independent dummy variables to eliminate when no data is available, wherein the modified XGBoost algorithm generates a predicted trajectory of resting and active phase of when there will be little to no day, or night activity levels of a patient;

determining a daytime threshold and a nighttime threshold from the data obtained during the one or more daytime and nighttime cycles by:

identifying one or more daytime and nighttime boundaries by:

selecting from at least one of physical activity, heart rate, or sleep status data;

temporally segmenting the physical activity, heart rate, or sleep status data to establish a circadian rhythm;

using at least one of a 2-mean, 5-mean, or K-nearest neighbor algorithm to determine the one or more daytime and nighttime boundaries; and identifying and predicting the personalized circadian rhythm.

\* \* \* \* \*